(12) United States Patent
Biancalani et al.

(10) Patent No.: US 9,402,466 B2
(45) Date of Patent: Aug. 2, 2016

(54) SANITIZING DEVICE FOR TOOTHBRUSHES

(71) Applicants: Tommaso Biancalani, Bagno a Ripoli (IT); Clemente Biancalani, Bagno a Ripoli (IT)

(72) Inventors: Tommaso Biancalani, Bagno a Ripoli (IT); Clemente Biancalani, Bagno a Ripoli (IT)

( * ) Notice: Subject to any disclaimer, the term of this patent is extended or adjusted under 35 U.S.C. 154(b) by 156 days.

(21) Appl. No.: 14/350,656

(22) PCT Filed: Oct. 11, 2012

(86) PCT No.: PCT/IB2012/055513
§ 371 (c)(1),
(2) Date: Apr. 9, 2014

(87) PCT Pub. No.: WO2013/054284
PCT Pub. Date: Apr. 18, 2013

(65) Prior Publication Data
US 2014/0286830 A1 Sep. 25, 2014

(30) Foreign Application Priority Data
Oct. 13, 2011 (IT) .................. FI2011A0225

(51) Int. Cl.
*A46B 17/06* (2006.01)
*A61L 2/18* (2006.01)

(52) U.S. Cl.
CPC .............. *A46B 17/065* (2013.01); *A61L 2/18* (2013.01); *A46B 2200/1066* (2013.01)

(58) Field of Classification Search
CPC ............................ A46B 17/065; A61L 2/18
See application file for complete search history.

(56) References Cited

U.S. PATENT DOCUMENTS

| | | | | |
|---|---|---|---|---|
| 1,743,646 A * | 1/1930 | Alderman, Jr. | ......... | A45D 44/00 206/209.1 |
| 3,342,544 A * | 9/1967 | Curiel | .................. | A61L 2/0005 132/310 |
| 3,884,635 A * | 5/1975 | Sloan | ..................... | A45D 44/18 206/209 |
| 3,904,362 A * | 9/1975 | DiPaolo | ................... | A61L 2/26 206/209 |
| 4,088,445 A * | 5/1978 | Ellis | ......................... | A61L 2/10 250/455.11 |
| 4,473,152 A * | 9/1984 | Jump, Jr. | ................. | A47K 1/09 206/209 |

(Continued)

FOREIGN PATENT DOCUMENTS

| | | |
|---|---|---|
| DE | 10048071 | 5/2001 |
| GB | 2462540 | 2/2010 |
| WO | 00/19880 | 4/2000 |

OTHER PUBLICATIONS

PCT International Search Report mailed on Feb. 13, 2013 for PCT/IB2012/055513 filed on Oct. 11, 2012 in the name of Saint-Gobain Glass France.

(Continued)

*Primary Examiner* — Regina M Yoo
(74) *Attorney, Agent, or Firm* — Steinfl & Bruno LLP

(57) ABSTRACT

A sanitizing device for toothbrushes is described. The device has a lower housing body, and a vessel for containing a sanitizing liquid being connected to the lower housing body in an upper position according to a vertical axis. The lower housing body has removable basins adapted to contain a head of the toothbrush substantially arranged along the vertical axis. The removable basins are hydraulically connected to the vessel for the controlled flowing down of the sanitizing liquid from the vessel to the basins. The lower housing body is removably associated to a cap in an upper position according to the vertical axis, the cap being cup-shaped to enclose the vessel and possible portions of the toothbrush that project upwards from the lower body.

19 Claims, 6 Drawing Sheets

(56) References Cited

U.S. PATENT DOCUMENTS

| | | | | |
|---|---|---|---|---|
| 4,585,119 A * | 4/1986 | Boyington | A46B 17/04 | 206/209 |
| 4,995,509 A * | 2/1991 | Kornfeind | A61L 2/18 | 206/205 |
| 5,185,532 A * | 2/1993 | Zabsky | A61L 2/10 | 250/455.11 |
| 5,487,877 A * | 1/1996 | Choi | A47K 5/00 | 222/192 |
| 5,566,823 A | 10/1996 | Summers | | |
| 5,690,214 A * | 11/1997 | Gaines | A47K 1/09 | 206/15.3 |
| 5,882,613 A | 3/1999 | Gipson, II | | |
| 6,119,854 A | 9/2000 | Prentice | | |
| 6,135,279 A | 10/2000 | Dryer | | |
| 6,171,559 B1 * | 1/2001 | Sanders | A46B 17/06 | 134/144 |
| 6,360,884 B1 * | 3/2002 | Smith | A47K 1/09 | 206/209.1 |
| 6,565,819 B1 * | 5/2003 | Herrera | A46B 17/06 | 422/26 |
| 6,601,699 B1 | 8/2003 | Naredo | | |
| D528,334 S * | 9/2006 | Starck | D6/534 | |
| 7,188,629 B2 * | 3/2007 | Mehes | A46B 17/00 | 132/310 |
| 7,951,343 B1 * | 5/2011 | Davis | A61L 2/18 | 206/209 |
| 8,906,297 B1 * | 12/2014 | Ament | A61L 2/07 | 422/26 |
| 2004/0025899 A1 * | 2/2004 | Pinsky | A61L 2/10 | 132/310 |
| 2005/0276736 A1 * | 12/2005 | Miller | A47K 1/09 | 422/300 |
| 2008/0210702 A1 * | 9/2008 | Lochinger | A47K 5/1217 | 221/7 |
| 2008/0307591 A1 * | 12/2008 | Farrell | A61C 17/3418 | 15/22.2 |
| 2011/0203069 A1 * | 8/2011 | Boorstein | A46B 17/04 | 15/247 |
| 2012/0279007 A1 * | 11/2012 | Boorstein | A46B 17/04 | 15/247 |

OTHER PUBLICATIONS

PCT Written Opinion mailed on Feb. 13, 2013 for PCT/IB2012/055513 filed on Oct. 11, 2012 in the name of Saint-Gobain Glass France.

* cited by examiner

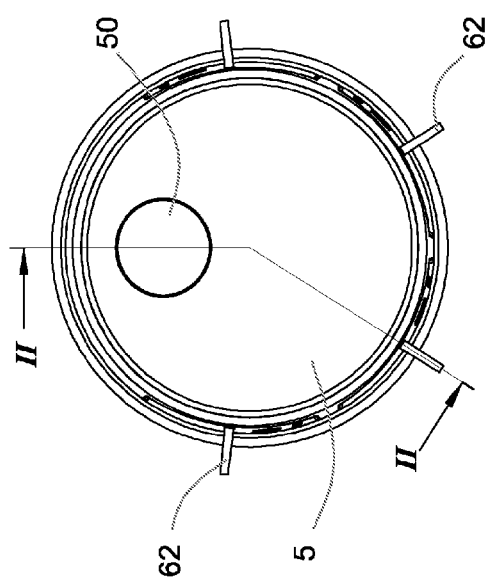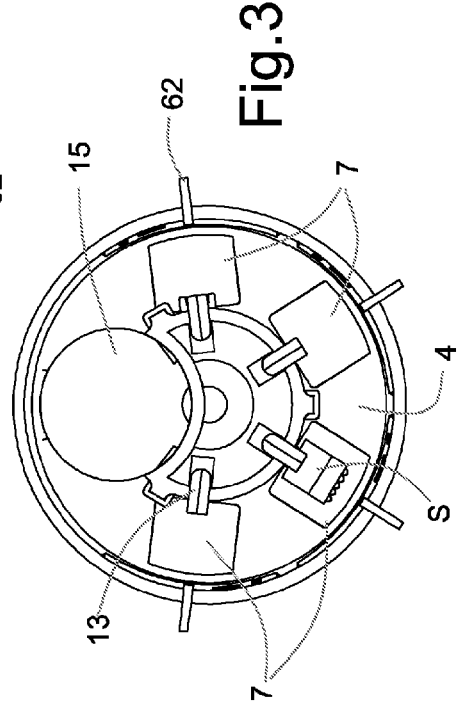

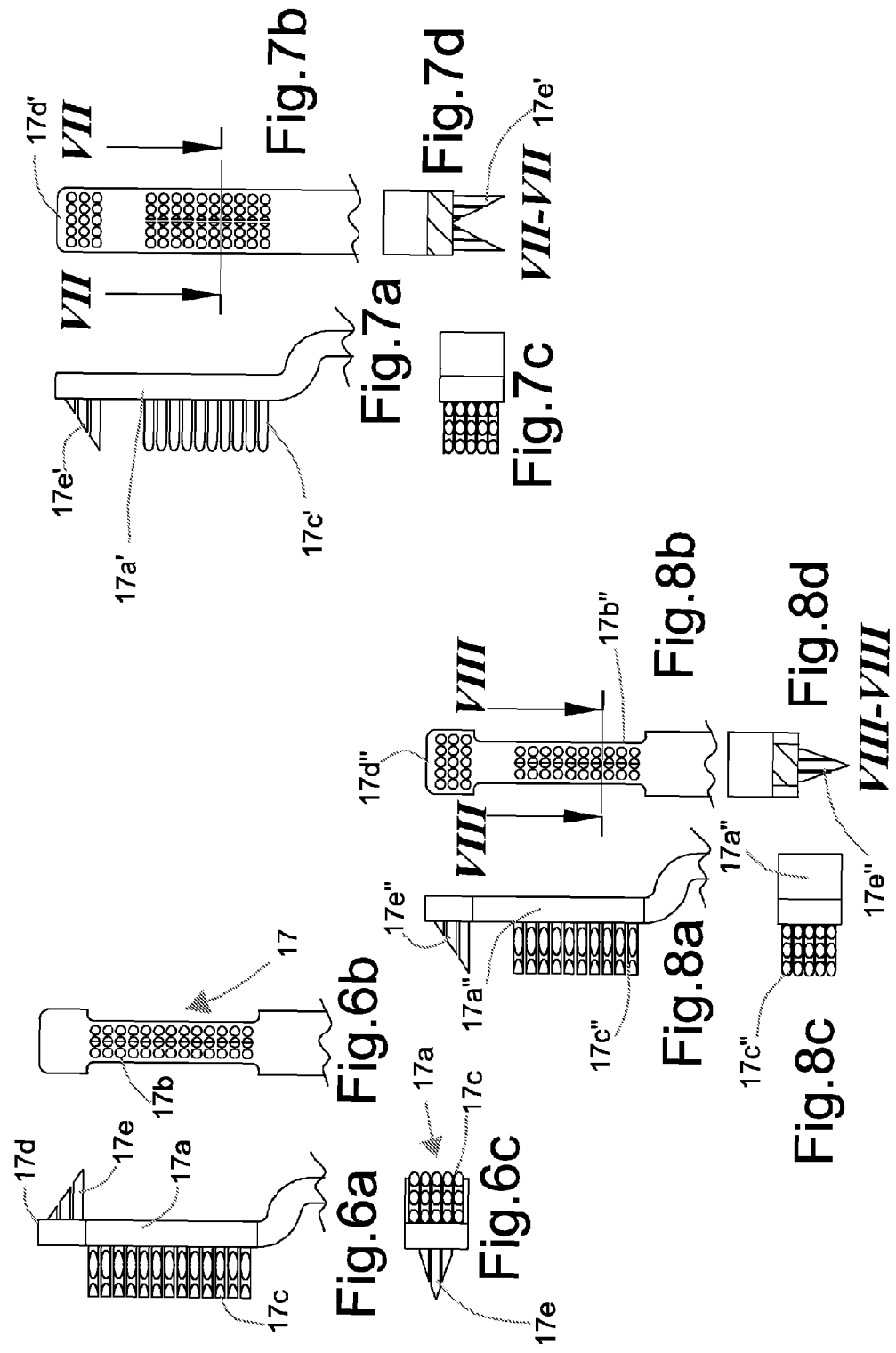

SANITIZING DEVICE FOR TOOTHBRUSHES

CROSS REFERENCE TO RELATED APPLICATIONS

The present application is the US national stage of International Patent Application PCT/IB2012/055513 filed on Oct. 11, 2012 which, in turn, claims priority to Italian Patent Application FI2011A000225 filed on Oct. 13, 2011.

The present invention refers to the field of sanitizing systems in general and more in particular it refers to a sanitizing device for toothbrushes.

It is common practice, after brushing teeth, to rinse the toothbrush under a jet of water (like that coming from taps) and to place it back in simple containers like, for example, glasses, bowls etc. However, simply rinsing with water is not sufficient to eliminate bacteria which nests in the bristles of the toothbrush. Again, in the containers where the toothbrushes are placed after being used, there is often dripping and the water trapped in the bristles stagnates, therefore, even in such containers there can be an environment that promotes the proliferation of the aforementioned bacteria and germs. If such pathogenic agents are not eliminated they are transmitted, through the toothbrush itself, to the oral cavity, where they can cause even serious pathologies.

Cleaning the toothbrush and the vessel where it is placed is therefore fundamental for the health of the oral cavity in general.

The U.S. Pat. No. 6,601,699 describes a system for holding a toothbrush with an antiseptic solution holder. The UK Patent Application No. GB2462540 relates to an apparatus for sterilising a part of an oral hygiene device such as the bristles of a toothbrush.

It is therefore a purpose of the present invention to provide a sanitizing device for toothbrushes in particular and for the oral cavity in general which obtains a perfect cleaning and disinfection of the toothbrush, and that is moreover practical and simple to use.

A further purpose of the present invention is to achieve a sanitizing device which makes it possible to contain many toothbrushes inside it and that is moreover compact so as to be easily placed in small spaces (such as, for example, on a basin).

Finally, another purpose of the present invention is to provide a device for cleaning the mouth comprising also a further toothbrush that is suitable for increasing the cleaning capability and therefore the correct sanitization of the oral cavity.

These and other purposes are achieved with a device for sanitizing and disinfecting toothbrushes and for sanitizing the oral cavity, the essential characteristics of which are defined in the first of the attached claims.

Further important characteristics are contained in the dependent claims.

BRIEF DESCRIPTION OF THE DRAWINGS

Further characteristics and advantages of the device according to the present invention shall become clearer from the following description of an embodiment thereof given as an example and not for limiting purposes with reference to the attached drawings in which:

FIG. 2 is a top view of the device of FIG. 1;

FIG. 3 is a top view of the device of FIGS. 1 and 2 without a cover lid; inside the device it is moreover possible to see a toothbrush;

FIGS. 6a to 6c represent in detail the head of a further toothbrush that is associated to the device of the previous figures;

FIGS. 7a to 7d represent in detail a head of a first variant of the further toothbrush of the previous figures from 6a to 6c;

FIGS. 8a to 8d represent in detail a head of a second variant of the further toothbrush of the previous figures from 6a to 6c and from 7a to 7d;

With reference to the aforementioned figures and in particular to FIGS. 1 to 4, the sanitizing device according to the invention comprises a lower housing body 1 that is suitable for being associated, at its top, to a cap 2 so as to form said device itself. As shown in the figures, but not for limiting purpose, the housing body 1 and the cap 2 have a substantially cylindrical shape and are arranged on top of one another along a main development axis X of the sanitizing device.

Figure 1:
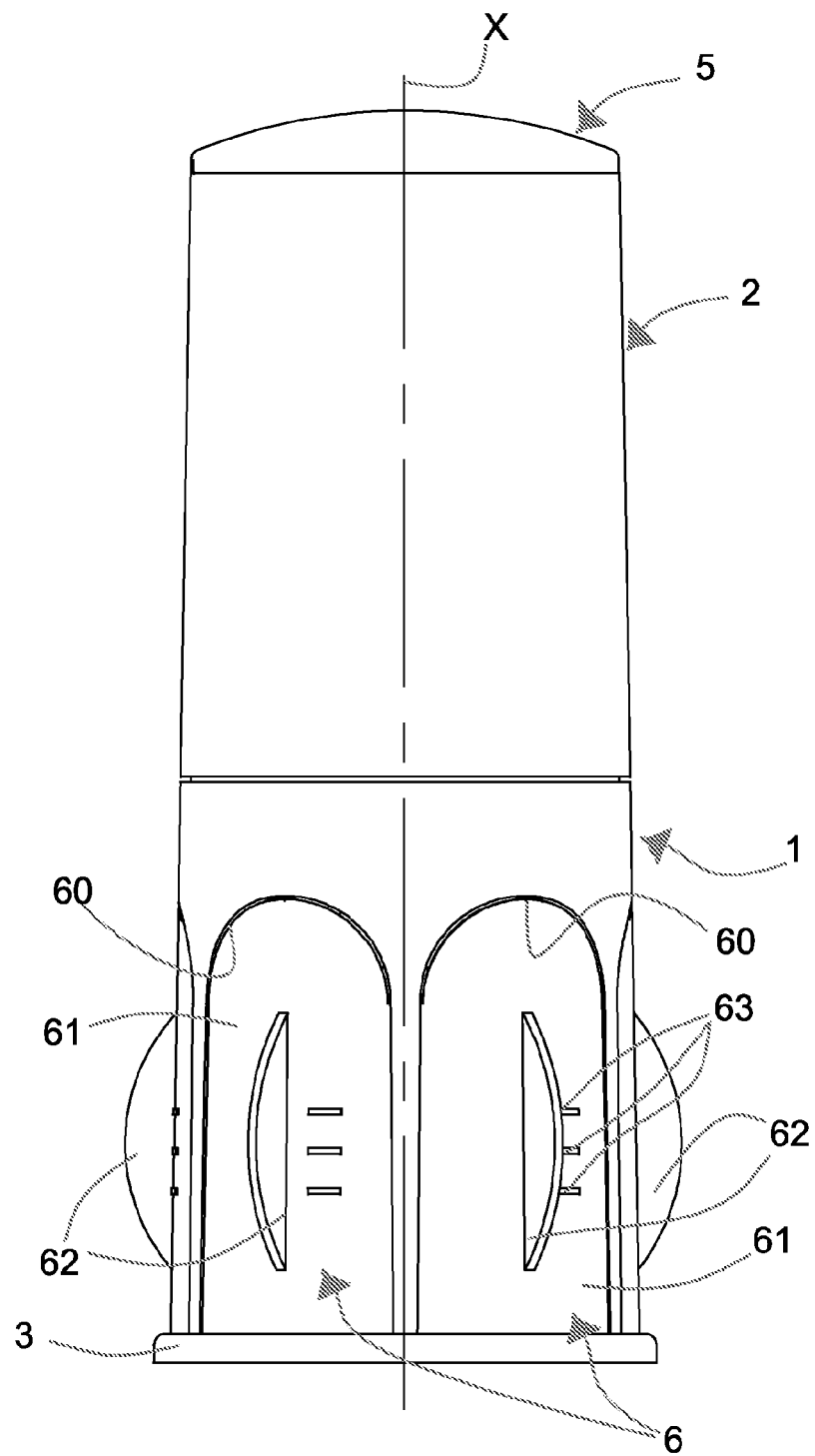
FIG. 1 shows the device according to the invention in a closed configuration.
Figure 4:
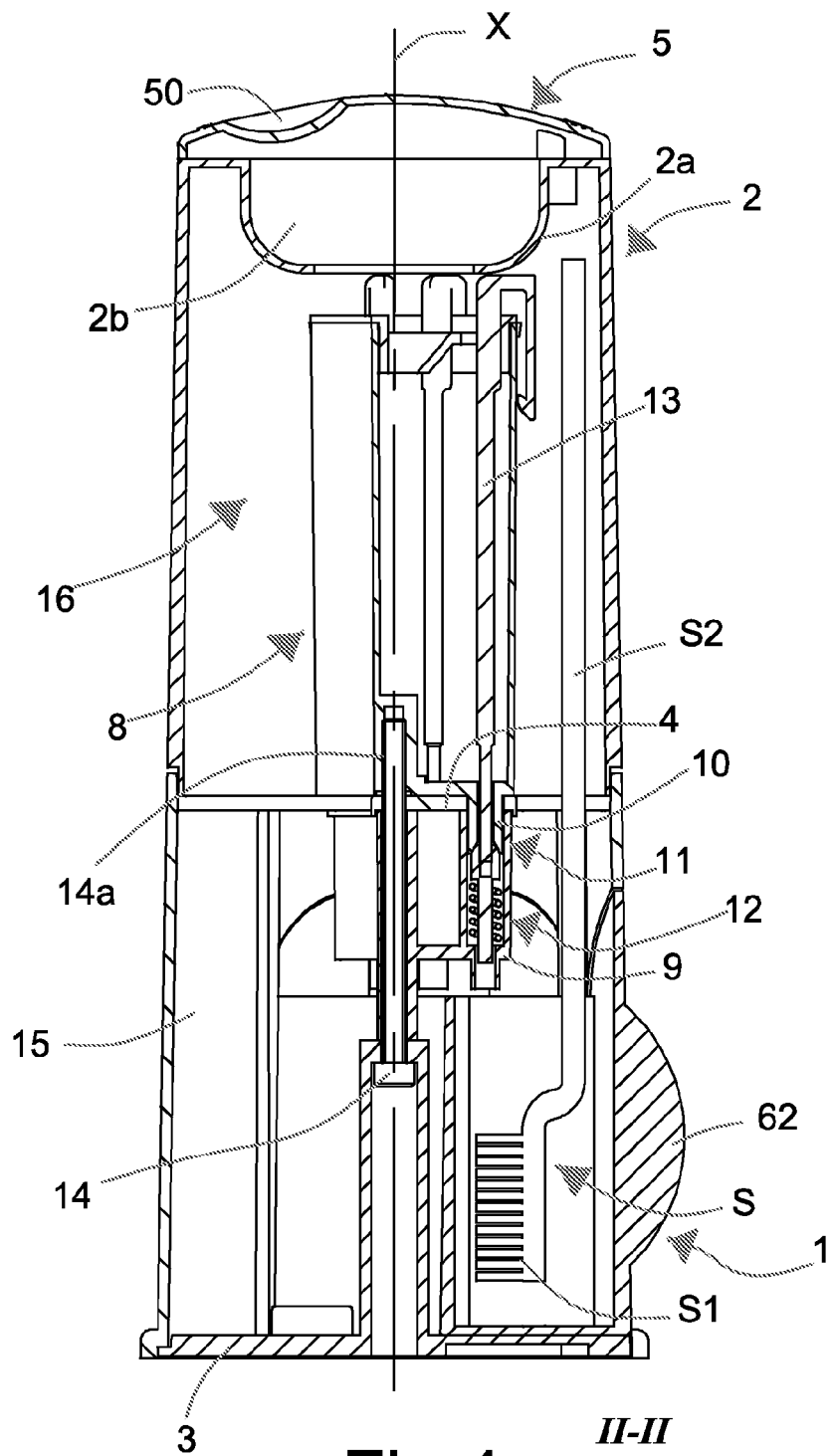
FIG. 4 shows a section view along the line II-II of FIG. 2 of the device according to the invention, inside which it is possible to see the toothbrush of FIG. 3, also represented in the section view.

The device is suitable for being rested on substantially flat surfaces, such as for example a bathroom shelf or wash basin, resting on its own basement 3, which closes the bottom of the housing body 1; at the top, the body is limited by a ceiling wall 4 (FIG. 4) that is arranged parallel and opposite to the basement 3. With particular reference to FIG. 4, in turn the cap 2 is closed at the top by a base wall 2a which, when the cap 2 is associated with the lower housing body 1, is arranged opposite with respect to the basement 3 itself. At the bottom, on the other hand, the cap 2 is open, so as to substantially have the shape of a cup (upside down when it is associated with the lower body 1).

Finally, above the cap 2, over the base wall 2a, a cover lid 5 is screwed on, so as to close the top of the device.

Figure 5B:
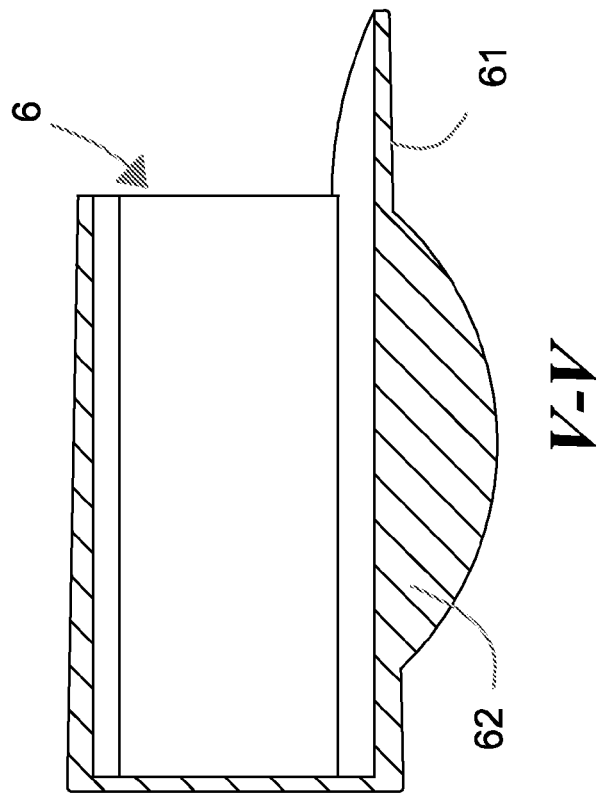
FIGS. 5a, 5b, are respectively a top view and a longitudinal section view (along the line V-V of FIG. 5a) of a basin of the device of the previous figures.
Figure 5A:
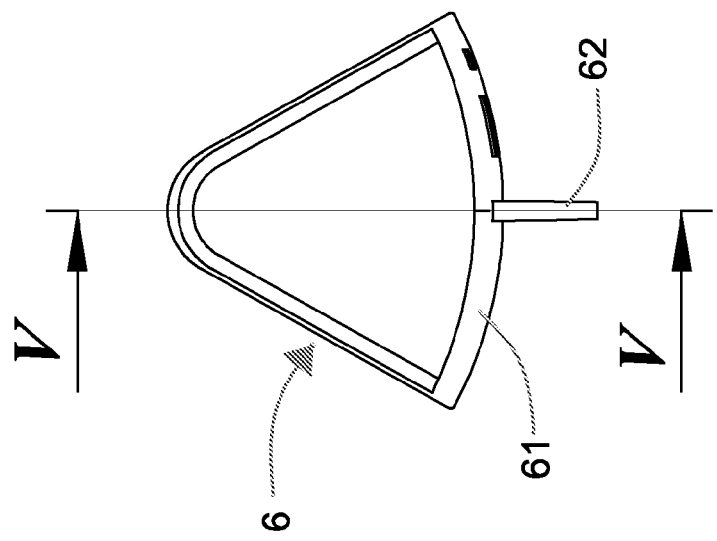

Going into detail, the lower housing body 1 has basins 6 (shown in detail in FIGS. 5a and 5b) that are arranged radially around the axis X. In the preferred configuration shown in the figures, the basins 6 are in a number of four, and are suitable for each housing a toothbrush S of the known type (as shall be explained more clearly in the following) or, possibly a head of an electric toothbrush. The basins 6 are removably inserted inside the body 1 and, for such a purpose, there are suitable openings 60 made on it, positioned near to the basement 3. Once the basins have been inserted in the suitable openings, an outer wall 61 of the basins themselves is arranged with continuity with respect to the outer surface of the housing body, defining therefore an outer surface of the device that is substantially uniform.

In order to assist the removal of the basins 6, handles 62 are made on the outer wall 61 so as to allow a user to easily hold it.

On the ceiling surface 4, at each basin 6, slits 7 are opened (FIG. 3) so as to allow the head S1 of the toothbrush S to pass through. In greater detail, as shown in FIG. 4, the head S1 of the toothbrush S is contained inside the basin 6 whereas the leg S2 extends above the ceiling surface 4 passing through the corresponding slit 7.

The basins 6 moreover have sizes such as to completely house the head of an electric toothbrush (not shown) inside them, for example in the vertical position.

Resting on the ceiling surface 4, above the housing body 1, a vessel 8 of a generic sanitizing liquid is fixed, which shall be described in greater detail in the rest of the description. Such a vessel 8 is hydraulically connected to the lower housing body 1 so as to allow the sanitizing liquid to flow down inside the basins 6.

In greater detail, on the ceiling surface 4 openings are made associated with the channels 9 which project inside the housing body 1 to the rim of each basin 6. Inside the channels 9 pipes 10 are engaged projecting from the vessel 8, creating a duct 11 which allows the aforementioned hydraulic connection. In order to prevent the accidental falling of liquid inside the basins 6, each duct 11 is intercepted by a check element 12 made up of a spring gasket, of the known type. In order to allow the opening of the check element 12, and consequently the falling of liquid, it is connected to a driving stem 13 which projects inside the vessel 8 and comes out at the top thereof. When the stem 13 is pushed manually downwards, the check element 12 opens, or rather it frees the duct 11 and the liquid can flow into the basins 6 below.

In order to evaluate the amount of liquid falling inside the basins 6 the wall 61 is preferably made of transparent material (such as glass or plexiglass) and level indicators, such as indication lines 63, are provided on it.

Advantageously, the stable connection between the vessel 8 and the lower housing body 1 is associated with a screw 14 arranged according to the axis X, which engages inside the ceiling surface 4 and is threaded in a suitable seat 14a made in the vessel 8. With particular reference now to FIGS. 2 and 3, the basins 6 are arranged adjacent to one another and have a crescent shape, in any case such as to leave a portion of the lower housing body 1 free from the basins 6 themselves. Therefore, such a free position defines a cavity 15 above which the ceiling surface 4 is interrupted or in any case has a suitable passage; it is therefore possible to insert from the top, inside such a cavity 15, objects such as, in particular and preferably, a tube of toothpaste.

As mentioned previously, above the lower housing body 1 a cap 2 is arranged, which being hollow inside, encloses the aforementioned components. Therefore a space 16 is created (FIG. 4) defined inside the cap 2 and defined at the bottom and at the top by the ceiling wall 4 and by the base wall 2a, respectively. Contained inside such a space 16 there are the legs of the toothbrushes, the vessel of liquid and the part of toothpaste which projects outside the housing body, allowing there to be a compact containment of all the necessary items for cleaning teeth.

Again, the base wall 2a has a U-shape or rather it obtains a recess 2b which, when the cap 2 is arranged on the housing body 1, faces upwards; such a recess 2b is therefore independent from the space 16 and is intercepted at the top by the cover lid 5. The recess 2b can therefore be accessed from outside by removing the cover lid 5. Such a removal is facilitated by the presence of a hole 50 (FIGS. 2 and 3) formed on the outer surface of the cover lid 5 itself; such a hole 50 promotes the engagement of the finger of a user and the necessary grip to impose an unscrewing rotation of the cover lid. The recess 2b has the shape and size such as to house a packet of dental floss.

Figure 9B:
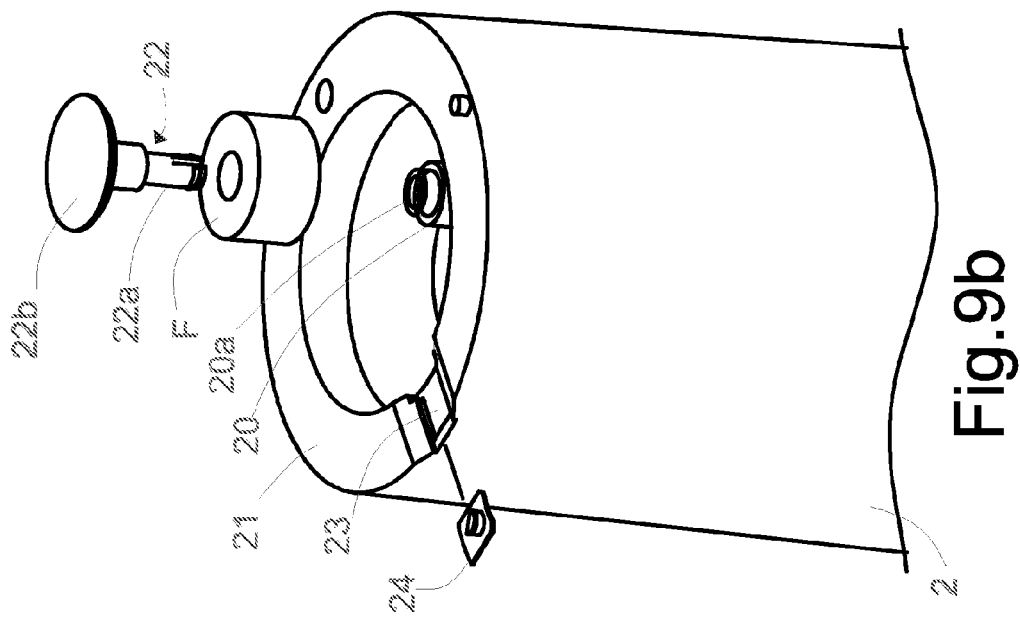
FIGS. 9a and 9b respectively show an assembled view and an exploded view of a variant embodiment of the vessel according to the invention, and in particular a variant of a cap of the vessel, which integrates rotatable support means and means for cutting the reel of dental floss.
Figure 9A:
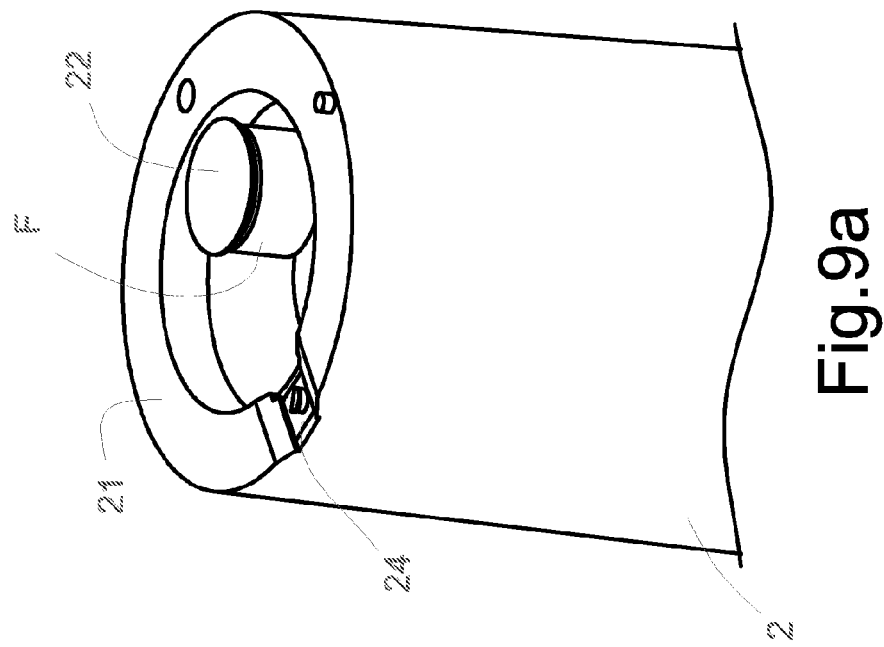

As shown in FIGS. 9a and 9b, the cap 2 can advantageously provide means for the rotatable support of a reel of dental floss and means for cutting the dental floss itself. In particular, the recess 2b provides, in this case, a pin 20 which rises from the bottom of the recess itself. The pin is suitable for rotatably housing a reel of dental floss F which is represented only schematically in the figure. In order to prevent the reel from accidentally coming out from the pin, such a variant embodiment of the present device can provide a mushroom shaped plug or thread stopper 22. The plug comprises a stem 22a which is inserted in a suitable hole 20a that is made in the head of the pin and a flat base 22b which projects from the stem and abuts, when the plug is mounted, against the flat face of the reel, preventing it from disengaging from the pin 20. On an upper edge 21 of the cap 2, or rather the edge that peripherally defines the recess 2b, there is a U-shaped throat 23; the throat has a flat lower face 23a on which a blade 24 is fixed for cutting the dental floss. Inside the recess 2b too, a suitable sanitizing liquid may be introduced in order to sanitise the dental floss and any further elements present inside the same recess.

In addition to the toothbrush S of the known type previously described, the device according to the invention also comprises a further toothbrush 17, 17', 17" represented in three different variants in figures from 6a to 8d. Such a further toothbrush 17, 17', 17" is necessary for the correct sanitization of the teeth and of the oral cavity, as shall be understood in the rest of the description.

With reference now to FIGS. 6a to 6c the further toothbrush 17 comprises a head 17a having a greater length with respect to the head S1 of a toothbrush of the known type S. The head 17a has a central section 17b that is narrower from where the first bristles 17c, which are arranged in parallel ranks, project. Beyond such a central section, on the opposite side with respect to that near the leg (only schematically shown in the figures) there is a point section 17d from where, on the opposite side with respect to the first bristles 17c, second bristles 17e project.

The first and second bristles are arranged at opposite sides of the head 17a of the toothbrush 17. Again, the first bristles 17c are tapered so as to define a triangular plan section, where the central bristles have greater length.

The first variant of the toothbrush 17' (FIGS. 7a to 7d) also has first and second bristles 17c', 17e' but they are arranged on the same side. Analogously to what has been described previously, the first bristles 17c' have a tapered outline.

The second variant of the toothbrush 17" (FIGS. 8a to 8d) has a central section 17b" that is narrower at a point section 17d" and from such sections respectively project first and second bristles 17c" and 17e", on the same side of the head 17a". Analogously to what has been described above the first bristles 17c" have a tapered dovetail outline. Concerning the second bristles 17e, 17e', 17e" these can have the same height or have a variable height.

Advantageously the device according to the present invention can be commercialised in two variants, or rather by itself or associated with a further toothbrush 17, 17', 17".

The operation of the device according to the invention should be clear from what has been previously described. Firstly, the user inserts a certain amount of water, preferably up to the first level (identified by the line 63 closest to the basement 3) in the basins 6. Afterwards the user removes the cap 2 and through the driving stems 13 he makes the sanitizing liquid contained inside the vessel 8 flow down inside the basins 6. Such a liquid can be selected from that preferred by the user or provided included with the device. In particular the liquid can be an antibacterial, antiseptic, anti-plaque liquid (for example a mouth wash). Once the liquid has been mixed with the water inside the basins 6 it is possible to dip the toothbrushes S, 17, 17' and 17" in such a mixture and arrange the tube of toothbrush and the dental floss in special spaces, the cavity 15 and the recess 2b, respectively. Also these last two products can be sold together with the device or purchased independently by the user who can choose the type of product he likes the most.

Once the toothbrush is dipped into the mixture of sanitizing liquid and water it is perfectly sanitized and ready to be used.

The device described, in the preferred variant embodiment, comprises four basins 6 to house the toothbrushes for two users. In particular, two basins 6 are provided having a mixture that is fifty percent of water and sanitizing liquid for dipping toothbrushes S of the known type, whereas the other two basins 6 are arranged with a mixture made up of two parts of sanitizing liquid and one part of water, for containing further toothbrushes 17, 17', 17''.

In order to promote the preparation of such mixtures with different ratios, on the wall 61 there are typically three lines 63 that are parallel and equally spaced apart.

The sanitization of the teeth with the device equipped with both toothbrushes of the known type S and further toothbrushes 17, 17', 17'' occurs according to the following procedure.

The user removes the cap 2 and takes the toothbrush of the known type S so as to brush his teeth in the traditional-type way, possibly also using dental floss contained in the recess 2b, after removing the cover lid 5.

Once the teeth have been cleaned, the toothbrush of the known type S is inserted back into the basin 6 where, when dipped into the mixture of fifty percent sanitizing liquid and water, it is sanitized and disinfected.

At this stage the user uses the further toothbrush 17, 17', 17'', extracting it from the respective basin 6. Since it is soaked in a mixture that is mainly sanitizing liquid, such a further toothbrush 17, 17', 17'' exerts a greater disinfecting action on the known type of toothbrush S since the bristles release on the teeth and in the oral cavity the mixture they are soaked in.

The first bristles 17c, 17c', 17c'', in particular thanks to their tapered shape, are inserted in the gaps between the teeth and in the gum spaces, penetrating in the areas in which usually other toothbrushes do not reach, due to their conformation.

Therefore the mixture of sanitizing liquid penetrates in the gaps and in the recesses of the oral cavity where it stays even for some hours, promoting not only the elimination of the pathogenic agents and of the bacteria but even the removal of pieces of food, thus preventing plaque, tooth decay, and other pathologies of the oral cavity. The basins can possibly be filled with mixtures using a different antibacterial liquid. For example, one basin containing a conventional toothbrush is filled with sanitizing liquid of the antibacterial type. In such a case a mixture of liquid and water or the pure liquid can be provided, as described above.

In the basin intended for containing the further toothbrush, on the other hand, antiseptic liquid can be introduced, such as, but not for limiting purposes, a mouth wash. Also in this case it is possible to use the pure liquid or the liquid mixed with water.

The device according to the present invention therefore achieves a complete sanitization of the oral cavity in a simple manner and can easily be understood by all categories of users. Moreover it can be adapted to the need or to the preferences of each user since it is possible to use it also with other products that are already available on the market.

The device is moreover extremely compact and linear so as to adapt to any environment without losing however the capability of containing inside it everything that is needed for cleaning teeth. Therefore this avoids having all the various products intended for cleaning teeth in different places with considerable saving in terms of space and time of use.

As previously mentioned, the device according to the invention can be sold separately or together with the toothbrush 17, 17', 17''.

Again the device according to the invention can have a different shape from the one described previously (for example it can have a substantially parallelepiped or polygonal shape). Moreover devices can be foreseen suitable for containing only two toothbrushes or, on the contrary, for containing a greater number of toothbrushes with respect to the variant with four toothbrushes previously described. For such a purpose the device will have a number of basins that is suitable for the number of toothbrushes it must contain.

As previously mentioned, the sanitizing liquid can be an antibacterial or antiseptic liquid, etc. Therefore a single liquid could be used to fill all basins or different liquids according to the type of toothbrush contained in each basin. For such a purpose many vessels 8 can be provided, hydraulically separated from one another, for containing different types of sanitizing liquid.

In addition to the toothbrushes previously described, the device is suitable for housing also the heads of electrical toothbrushes or small sized electrical toothbrushes, tools for cleaning teeth in general or small dentist tools such as, for example, a mirror, a probe, a periodontal probe, etc.

Again, in case the cap 2 comprises means for rotatably supporting and cutting the dental floss, the sanitizing vessel according to the invention achieves a surprising result in terms of integration of the various products necessary for sanitizing the oral cavity. The user indeed finds all he needs for cleaning the oral cavity in one place and inside the vessel itself. The user can moreover buy only the reel of dental floss, sold for example in the form of handy refill packets, with a substantial saving in terms of money and raw material, indeed such as the plastic necessary for making the boxes for containing the dental floss, and advantages for the environment.

The materials used for the device can be those used in the field of bathroom furniture, such as for example plastic, metal, glass, etc.

The present invention has been described with reference to preferred embodiments thereof. It should be understood that there can also be other embodiments which belong to the same inventive core, all covered in the field of protection of the following claims.

The invention claimed is:

1. A sanitizing device for toothbrushes, comprising:
a lower housing body, and
a vessel for containing a sanitizing liquid being connected to said lower housing body in an upper position according to a vertical axis,
wherein:
said lower housing body comprises removable basins adapted to contain a head of said toothbrush substantially arranged along said vertical axis and said lower housing body further comprises openings for insertion of said removable basins,
said removable basins are hydraulically connected to said vessel for a controlled flowing down of said sanitizing liquid from said vessel to said removable basins,
said lower housing body is removably associated to a cap in an upper position according to said vertical axis, and
said cap is cup-shaped to enclose said vessel and possible portions of said toothbrush that project upwards from said lower housing body.

2. The sanitizing device according to claim 1, wherein:
said vessel is hydraulically connected to said removable basins via ducts, and check elements intercepting said ducts to control flowing down of said sanitizing liquid inside said removable basins.

3. The sanitizing device according to claim 2, wherein:
said lower housing body further comprises a basement and a ceiling wall presenting slits for insertion of said head in each of said removable basins.

4. The sanitizing device according to claim 3, wherein:
said vessel rests on said ceiling wall in an upper position with respect to said lower housing body, and
openings for the passage of said ducts are also formed on said ceiling wall in correspondence of each of said removable basins.

5. The sanitizing device according to claim 2, wherein:
said check elements are driven each by a stem that projects out from said vessel according to said vertical axis, said stem being associated to elastic check means, and
flowing down of said sanitizing liquid in each of said removable basins corresponds to compression of said elastic check means.

6. The sanitizing device according to claim 1, wherein said lower housing body further comprises a cavity adapted to contain a tube of toothpaste in a vertical position along said vertical axis.

7. The sanitizing device according to claim 6, wherein:
said cap comprises a base wall on which a recess is formed, said recess being adapted to contain a product for tooth cleaning.

8. The sanitizing device according to claim 7, wherein the product for tooth cleaning is dental floss and said cap integrates means for rotatably engaging with a reel of said dental floss and means for cutting said dental floss.

9. The sanitizing device according to claim 8, wherein:
said means for rotatably engaging with said reel of dental floss comprise a pin, said pin projecting inside said recess, and
said means for cutting said dental floss in turn comprising a blade fixed within a throat open on an outer peripheral edge of said recess.

10. The sanitizing device according to claim 7, wherein said recess is intercepted by a cover lid which is associated to said cap in an upper position according to said vertical axis.

11. The sanitizing device according to claim 6, wherein said cavity is a portion of said lower housing body free from said removable basins.

12. The sanitizing device according to claim 1, further comprising a toothbrush.

13. The sanitizing device according to claim 1, further comprising a toothbrush, the toothbrush comprising a first group of bristles and a separate second group of bristles, wherein bristles of the first group are arranged in parallel ranks and project from a central portion of a head of said toothbrush, and wherein bristles of the second group are arranged on said head in an upper position with respect to said bristles of the first group.

14. The sanitizing device according to claim 13, wherein said bristles of the first group present i) a tapered outline, or ii) at least one rank of bristles higher than other ranks.

15. The sanitizing device according to claim 13, wherein said first and second groups of bristles project from opposite sides of said head.

16. The sanitizing device according to claim 1, wherein each of said removable basins comprises a transparent outer wall on which level indicators of said sanitizing liquid are provided.

17. The sanitizing device according to claim 16, wherein handles project from said transparent outer wall of each removable basin in order for a user to easily hold the removable basins.

18. A sanitizing device for toothbrushes, comprising:
a lower housing body, and
a vessel for containing a sanitizing liquid being connected to said lower housing body in an upper position according to a vertical axis,
wherein:
said lower housing body comprises removable basins adapted to contain a head of said toothbrush substantially arranged along said vertical axis,
said removable basins are hydraulically connected to said vessel for a controlled flowing down of said sanitizing liquid from said vessel to said removable basins,
said lower housing body is removably associated to a cap in an upper position according to said vertical axis, and
said cap is cup-shaped to enclose said vessel and possible portions of said toothbrush that project upwards from said lower housing body;
wherein each of said removable basins comprises a transparent outer wall on which level indicators of said sanitizing liquid are provided.

19. The sanitizing device according to claim 18, wherein handles project from said transparent outer wall of each removable basin in order for a user to easily hold the removable basins.

* * * * *